United States Patent [19]

Powles et al.

[11] Patent Number: 5,746,724
[45] Date of Patent: May 5, 1998

[54] ASPIRATION NEEDLE APPARATUS INCORPORATING ITS OWN VACUUM AND METHOD AND ADAPTER FOR USE THEREWITH

[75] Inventors: Trevor J. Powles, Surrey, United Kingdom; Mir A. Imran, Los Altos Hills, Calif.; Baber Syed, Palo Alto, Calif.; Deepak R. Gandhi, San Jose, Calif.

[73] Assignee: Advanced Cytometrix, Inc., Sunnyvale, Calif.

[21] Appl. No.: 631,537

[22] Filed: Apr. 12, 1996

Related U.S. Application Data

[63] Continuation-in-part of Ser. No. 504,928, Jul. 20, 1995, Pat. No. 5,653,694, which is a continuation-in-part of Ser. No. 421,064, Apr. 13, 1995, abandoned.

[51] Int. Cl.$^6$ ............................ A61M 5/00; A61M 5/31
[52] U.S. Cl. ...................... 604/240; 604/201; 604/411; 128/763; 128/764
[58] Field of Search .................... 604/35, 36, 140, 604/86, 88, 190, 201, 204, 206, 240, 217, 185, 272, 273, 403, 411–414, 415; 128/752, 763–765, 770

[56] References Cited

U.S. PATENT DOCUMENTS

| | | | |
|---|---|---|---|
| 3,484,849 | 12/1969 | Huebner et al. | 604/413 |
| 3,724,460 | 4/1973 | Gomez et al. | 604/88 |
| 3,797,488 | 3/1974 | Hurschman et al. | 604/136 |
| 4,935,020 | 6/1990 | Broden | 604/411 |
| 5,017,191 | 5/1991 | Yamada et al. | 604/243 |
| 5,128,048 | 7/1992 | Stewart et al. | 210/749 |
| 5,358,501 | 10/1994 | Meyer | 604/414 |

Primary Examiner—Michael Powell Buiz
Assistant Examiner—A. T. Nguyen
Attorney, Agent, or Firm—Flehr Hohbach Test Albritton & Herbert LLP

[57] ABSTRACT

An aspiration needle apparatus for collecting cell samples from tissue comprising a vacuum container having an enclosed evacuated space evacuated to a subambient pressure and sealed by a penetrable diaphragm. An adapter is provided having a recess which is adapted to receive the vacuum container. A needle assembly is carried by the adapter and has a distal extremity serving as an aspiration needle to collect the cell sample. The proximal extremity of the needle assembly is disposed in said recess and is capable of penetrating the diaphragm of the vacuum container to couple the evacuated space to the flow passage of the needle assembly to supply a subambient pressure to the distal extremity of the needle assembly. An on-off mechanism is carried by the adapter and includes a member engaged by the vacuum container and mounted in the recess for axial movement in the recess. A coil spring is disposed within the recess and engages the member and yieldably urges the member and the vacuum container in a direction out of the recess. A detent assembly is secured to the member for sequentially retaining the member in a first forwardmost position and a second rearwardmost position. In the first position the needle assembly penetrates the diaphragm of the vacuum container to supply a subambient pressure to the needle assembly and in the second position the needle assembly is free of the diaphragm so that subambient pressure is no longer supplied to the needle assembly.

10 Claims, 6 Drawing Sheets

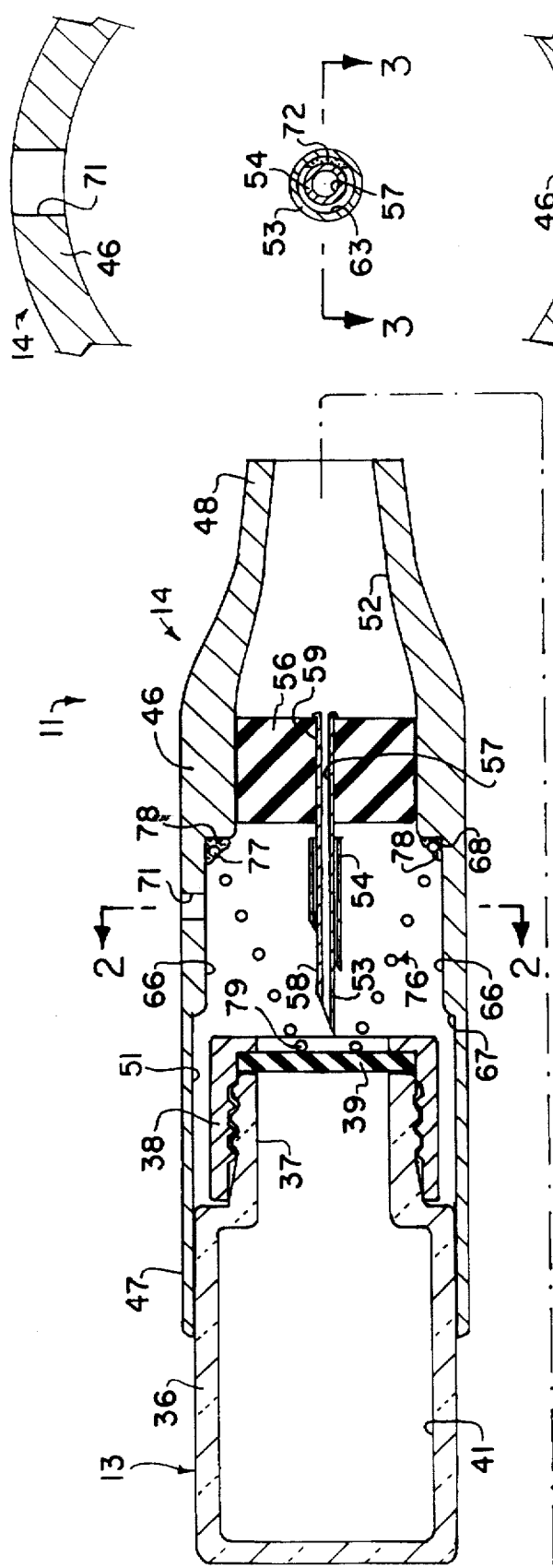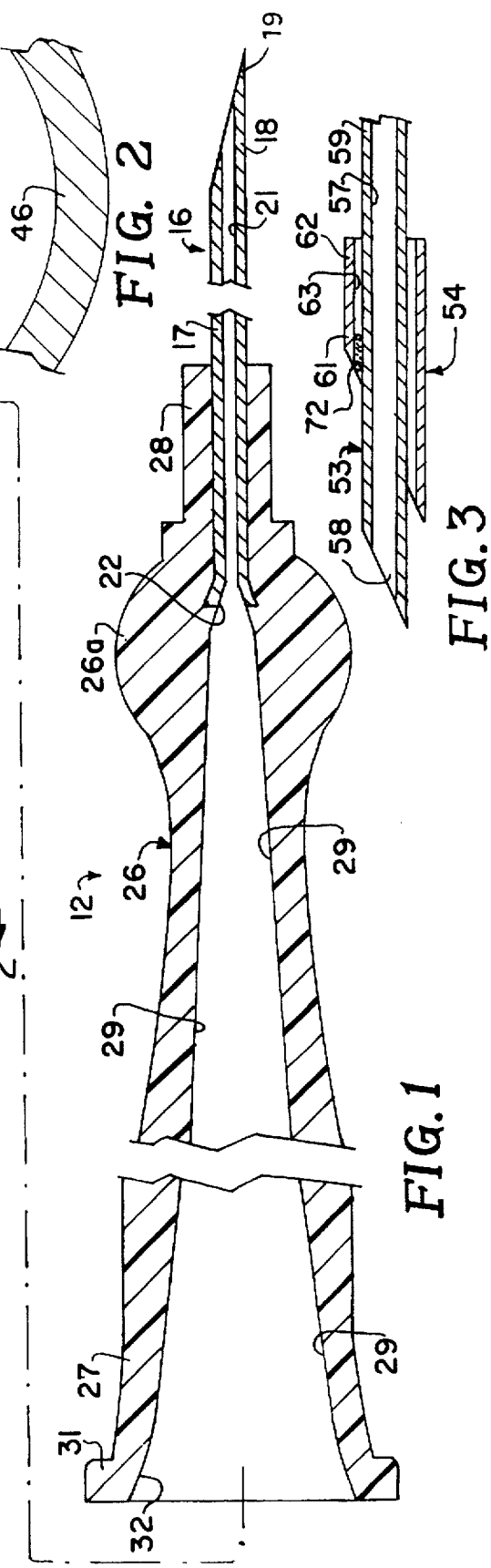
FIG. 1
FIG. 2
FIG. 3

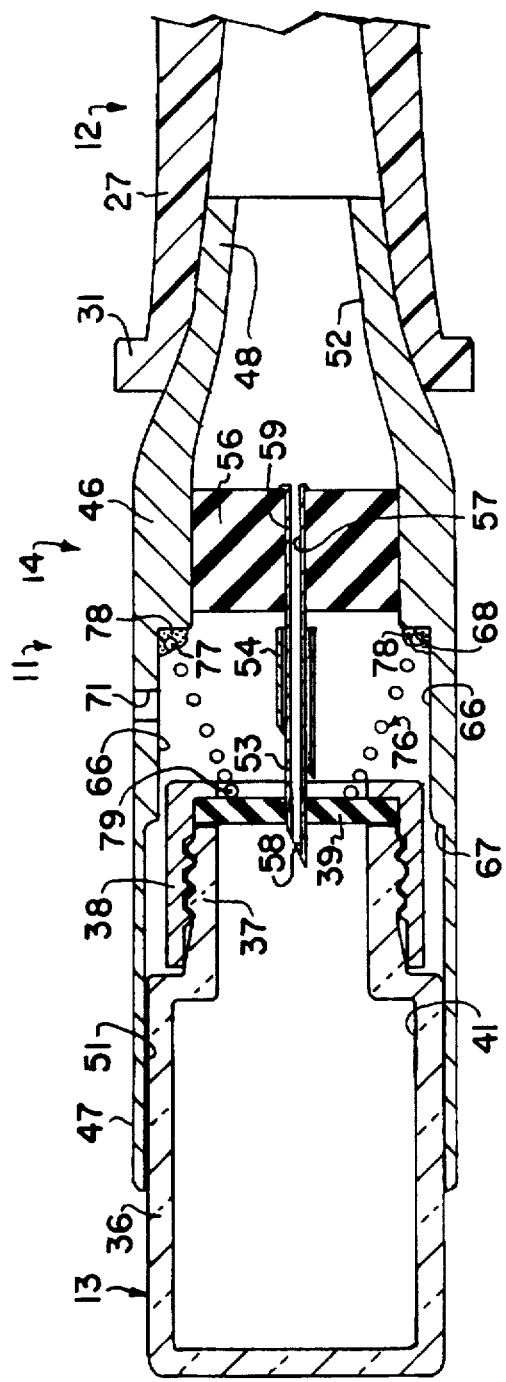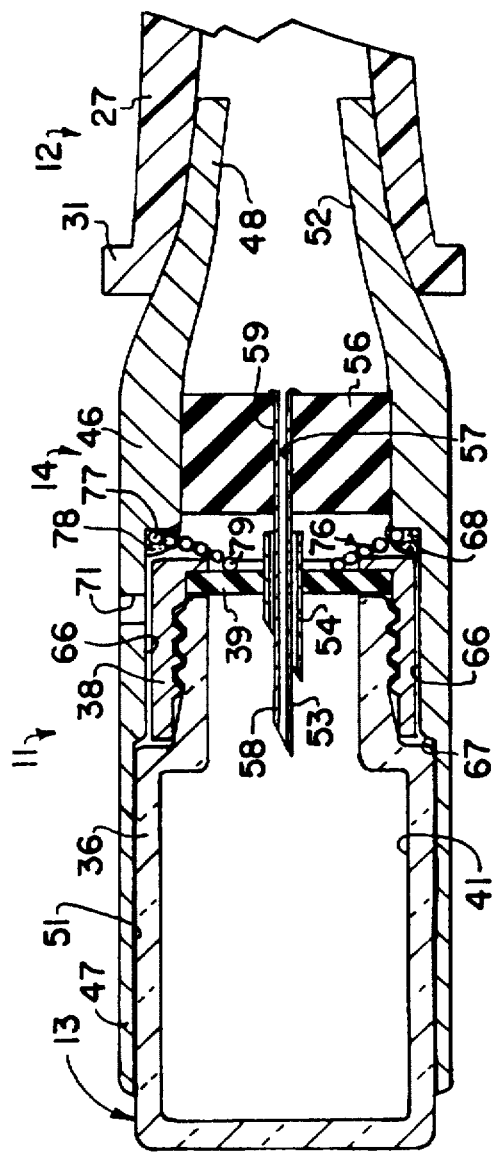

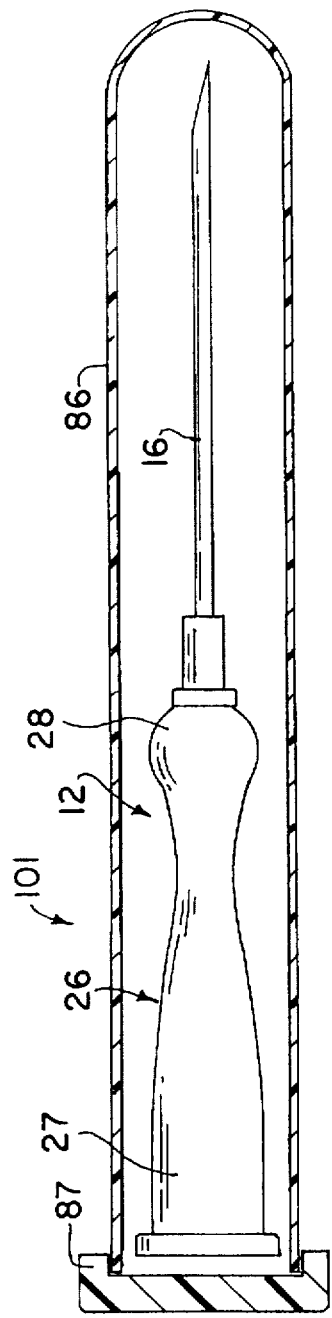
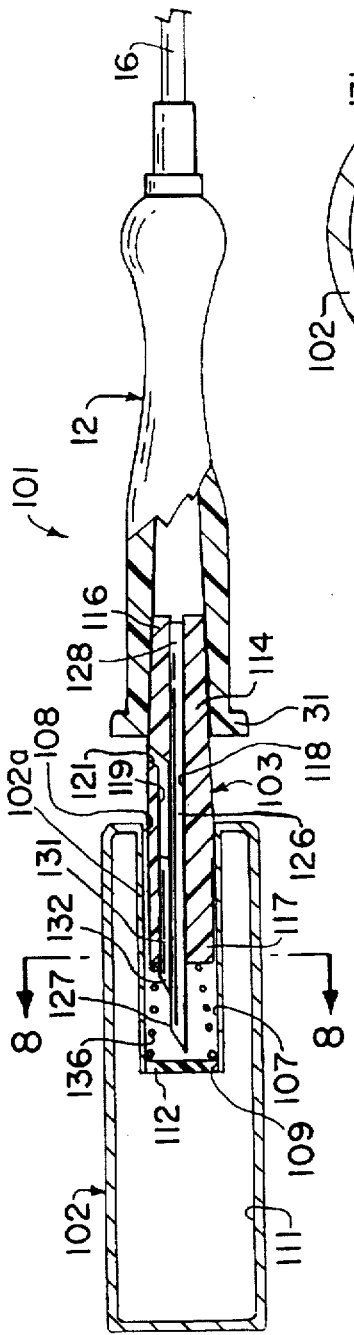
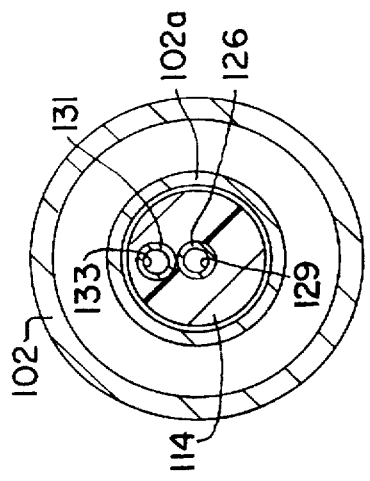
FIG. 6
FIG. 7
FIG. 8

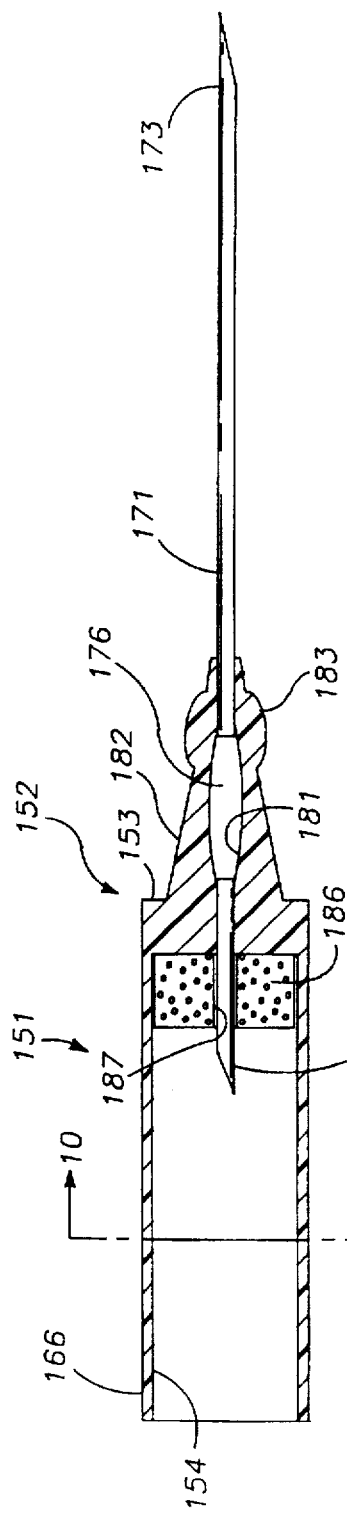
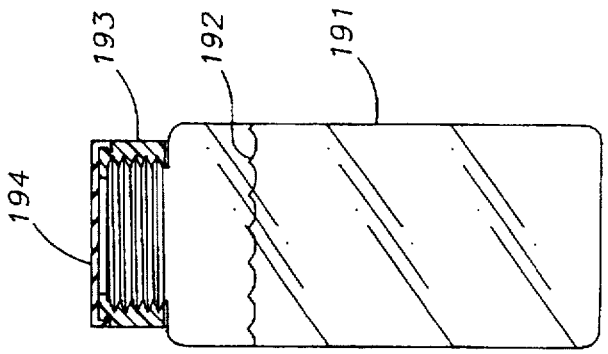
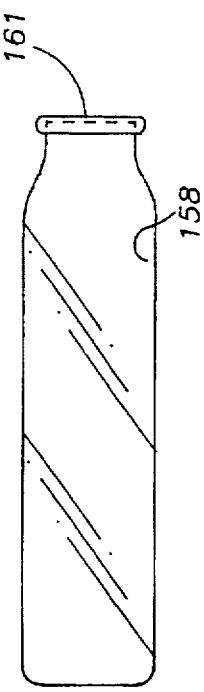
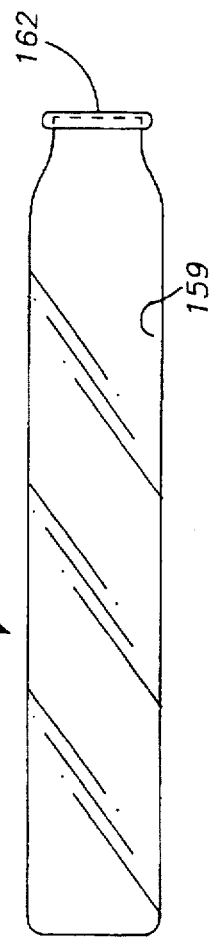
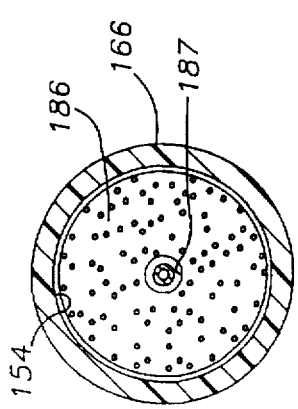

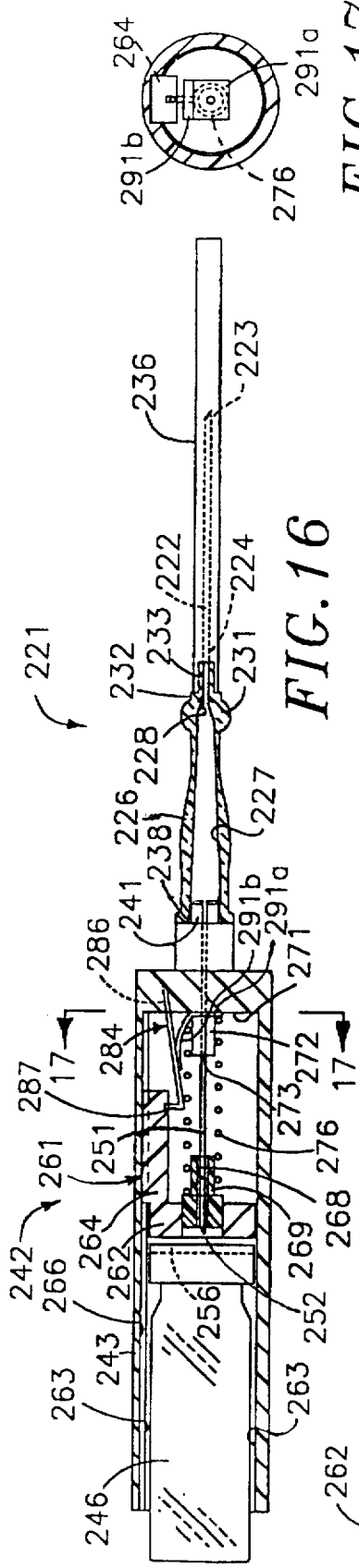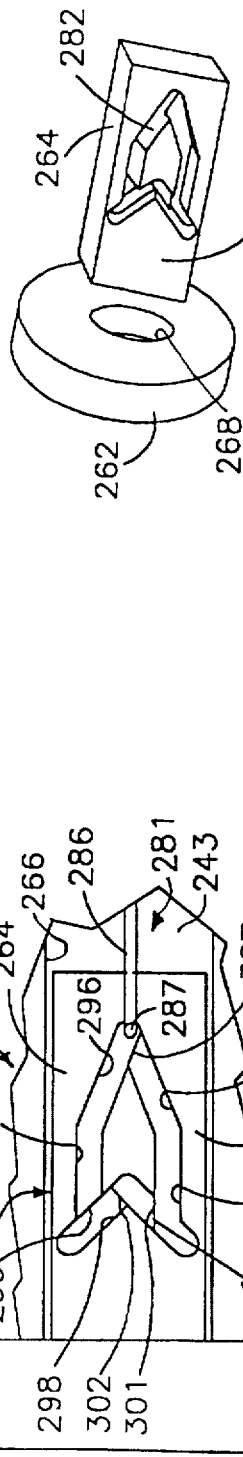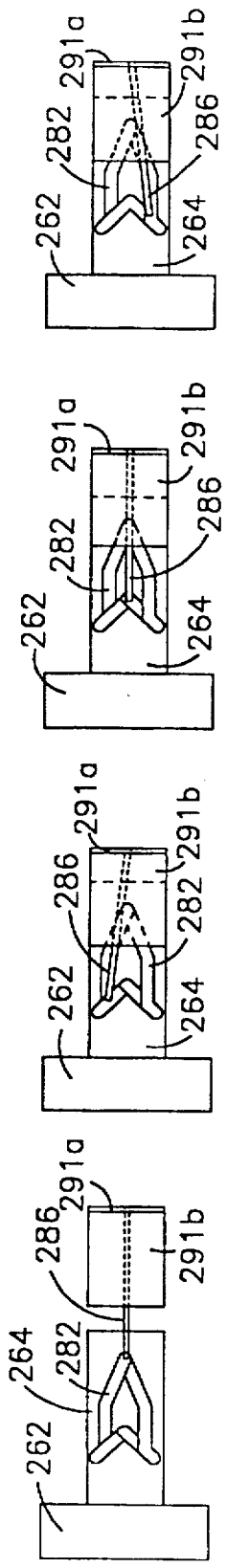

ASPIRATION NEEDLE APPARATUS INCORPORATING ITS OWN VACUUM AND METHOD AND ADAPTER FOR USE THEREWITH This application is a continuation-in-part of application Ser. No. 08/504,928 filed Jul. 20, 1995, now U.S. Pat. No. 5,653,694, which is a continuation-in-part of application Ser. No. 08/421,064 filed on Apr. 13, 1995.

In fine needle aspiration technology, there has been a need for applying a vacuum to the needle to accomplish the aspiration. Typically this has been accomplished by use of a syringe and in certain occasions by the application of a vacuum to the needle by a vacuum pump under the control of the physician performing the aspiration procedure. There is a need for a simplified apparatus for accomplishing fine needle aspiration.

In general, it is an object of the present invention to provide an aspiration needle apparatus incorporating its own vacuum and a method and adapter for use therewith.

Another object of the invention is to provide a removable adapter which can be utilized for mating an aspiration needle to a vacuum container.

Another object of the invention is to provide an apparatus and method and adapter of the above character for use therewith which makes it possible to readily establish a vacuum condition in the needle apparatus and to thereafter break the vacuum.

Another object of the invention is to provide an apparatus and method and adapter of the above character in which an on-off mechanism is provided with the adapter to facilitate the establishing of the vacuum condition.

Another object of the invention is to provide an adapter of the above character which can be used repeatedly.

Another object of the invention is to provide an aspiration needle apparatus of the above character in which first and second needles are provided for first communicating with the vacuum and thereafter for breaking the vacuum.

Another object of the invention is to provide an aspiration needle apparatus of the above character in which only a single needle is required.

Another object of the invention is to provide an aspiration needle apparatus and method of the above character in which the specimen cell sample can be sucked out of the needle through a second vacuum container along with a medium.

Another object of the invention is to provide an aspiration needle apparatus and method of the above character in which the cell sample along with the medium can be shipped in the second vacuum container to a laboratory for analysis.

Additional objects and features of the invention will appear from the following description in which the preferred embodiments are set forth in detail in conjunction with the accompanying drawings.

FIG. 1 is a side-elevational view in section of an aspiration needle apparatus incorporating its own vacuum which includes the aspiration needle, an adapter and a vacuum container.

FIG. 2 is an enlarged cross-sectional view taken along the line 2—2 of FIG. 1.

FIG. 3, is a cross-sectional view taken along the line 3—3 of FIG. 2.

FIG. 4 is a view similar to that shown in FIG. 1 but showing the vacuum in the vacuum container being applied to the needle.

FIG. 5 is a view similar to FIG. 4 but showing the vacuum to the needle being broken.

FIG. 6 is a side-elevational view in section showing an aspiration needle with a collected cell sample in a sealed container for transportation to a laboratory.

FIG. 7 is a side-elevational view of another embodiment of the present invention.

FIG. 8 is a cross sectional view taken along the lines 8—8 of FIG. 5.

FIG. 9 is a side-elevational view in section of another embodiment of an aspiration needle apparatus incorporating the present invention.

FIG. 10 is a cross sectional view taken along the line 10—10 of FIG. 9.

FIG. 11 is a side-elevational view of a small vacuum container utilized with the apparatus shown in FIG. 9.

FIG. 12 is a side-elevational view of a large vacuum container used with the apparatus shown in FIG. 9.

FIG. 13 is a side-elevational view of a bottle containing a medium for use with the apparatus shown in FIG. 9.

FIG. 16 is a side-elevational view partially in cross-section of an apparatus incorporating another embodiment of the invention.

FIG. 17 is a cross-sectional view taken along the line 17—17 of FIG. 16.

FIG. 18 is a greatly enlarged cross-sectional view taken along the line 18—18 of FIG. 17.

FIG. 19 is an isometric view of the member which is slidably mounted in the cylindrical recess in the adapter shown in FIG. 16.

FIGS. 20A, 20B, 20C and 20D are illustrations or cartoons showing the manner in which the detent mechanism incorporating the adapter shown in FIG. 16 functions.

Figures 14, 15:
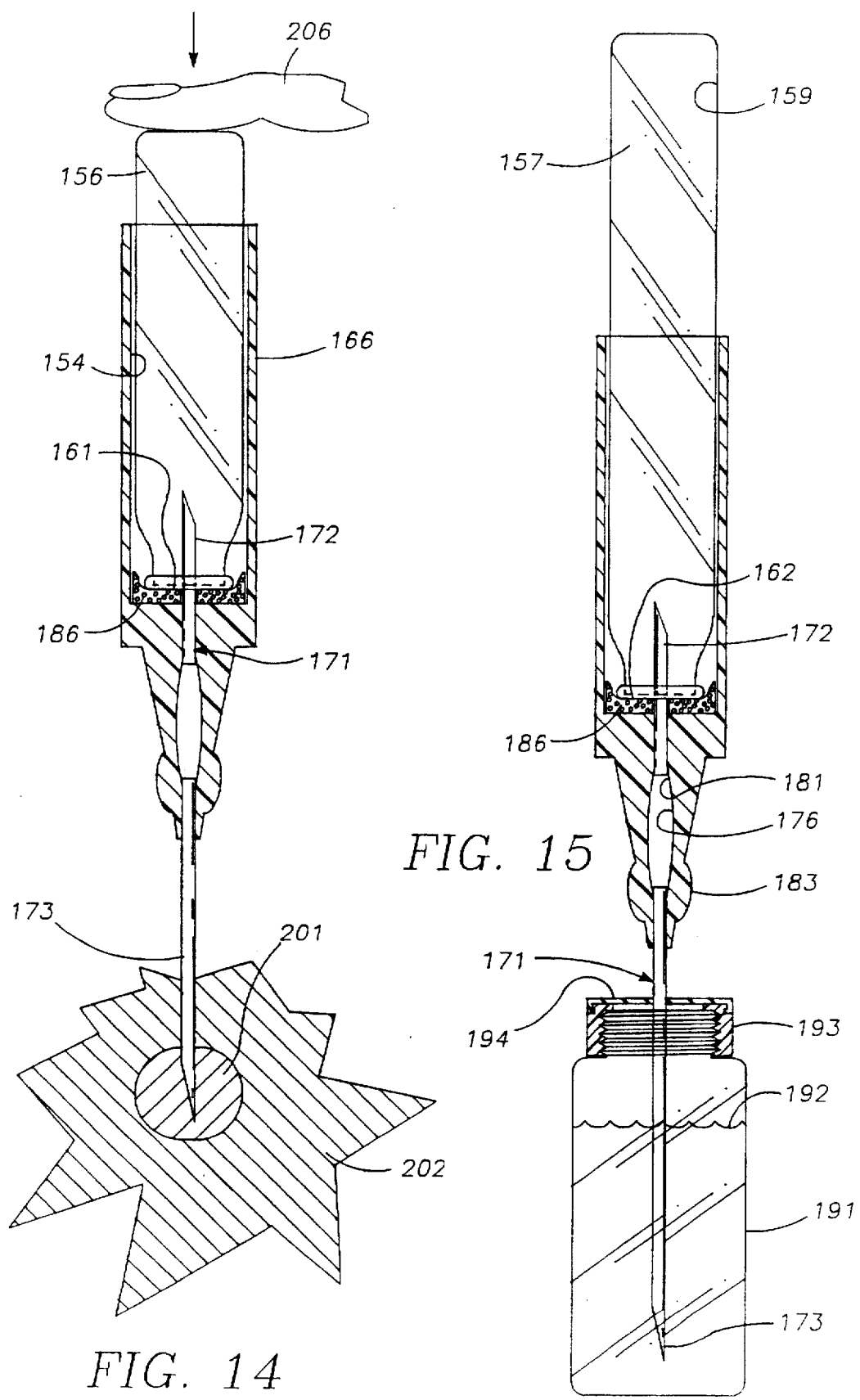
FIG. 14 is an illustration showing the manner in which the aspiration needle apparatus shown in FIGS. 9 through 11 can be utilized for collecting a cell sample in tissue as for example from a tumor in the tissue.
FIG. 15 is an illustration showing the manner in which the cell sample collected in the needle apparatus shown in FIG. 14 is sucked out of the needle along with a medium and into the large vacuum container shown in FIG. 12 with the medium being taken from the container shown in FIG. 13.

In general, an aspiration needle apparatus for collecting cell samples from tissue comprises a vacuum container having an enclosed evacuated space evacuated to a subambient pressure and sealed by a penetrable diaphragm. An adapter is provided having a recess which is adapted to receive the vacuum container. Needle means is carried by the adapter and has a distal extremity serving as an aspiration needle to collect the cell sample. The proximal extremity of the needle means is disposed in the recess and is capable of penetrating the diaphragm of the vacuum container to couple the evacuated space to the flow passage of the needle means to supply a subambient pressure to the distal extremity of the needle means. An on-off mechanism is carried by the adapter and includes a member engaged by the vacuum container and mounted in the recess for axial movement in the recess. Yieldable means is disposed within the recess and engages the member and yieldably urges the member and the vacuum container in a direction out of the recess. Detent means is secured to the member for sequentially retaining the member in a first forwardmost position and a second rearwardmost position. In the first position the needle means penetrates the diaphragm of the vacuum container to supply a subambient pressure to the needle means and in the second position the needle means is free of the diaphragm so that subambient pressure is no longer supplied to the needle means.

More in particular as shown in FIGS. 1–3 of the drawings, the aspiration needle apparatus 11 incorporating its own vacuum consists of an aspiration needle 12, a vacuum container 13 and an adapter 14 for mating the vacuum container 13 to the aspiration needle 12.

The aspiration needle 12 is of the type described in copending application Ser. No. 08/228,551 filed Apr. 15, 1994, U.S. Pat. No. 5,645,537, consisting of a rigid elongate tubular member 16 formed of a suitable material such as stainless steel having a length of 2 to 8 centimeters and of a suitable diameter as for example 23 gauge. The rigid elongate tubular member 16 is provided with proximal and distal extremities 17 and 18 in which the distal extremity is sharpened to form a needle point. The rigid elongate tubular member 16 is provided with a flow passage 21 extending from the distal extremity 18 to the proximal extremity 17. The proximal extremity 17 is flared outwardly to provide a funnel-shaped recess 22 leading into the flow passage 21.

A body 26 is mounted on the proximal extremity 17 of the rigid tubular member 16 and is formed of a suitable transparent plastic, as for example polycarbonate or acrylic. The body 26 is provided with proximal and distal extremities 27 and 28. The body 26 is provided with a conical chamber 29 extending from the proximal extremity 27 to the distal extremity 28. The body 26 is provided with a spherical enlarged portion 26a which circumscribes the conical chamber 29 in the region immediately adjacent the funnel shaped recess 22 which serves as a convex lens to magnify that portion of the container for viewing aspirate as hereinafter described. The body 26 is provided with a hub 31 on the proximal extremity 27 that has a tapered conical recess 32 which adjoins the conical chamber 29. The body 26 is provided with an annular recess 33 proximal of the enlarged portion 26a which is adapted to be engaged by fingers of the hand for controlling and movement of the needle for a purpose hereinafter described.

The vacuum container 13 is in the form of a vacuum bottle 36 formed of a suitable material such as glass. The glass bottle is of a conventional construction and is generally cylindrical in shape and is provided with a neck 37 of reduced diameter that has been threaded to receive a threaded cap 38. The cap 38 is provided with a self-sealing diaphragm or membrane 39 formed of a suitable self-sealing elastomeric material which can be readily penetrated by a conventional surgical needle. The vacuum container 13 encloses an evacuated space 41 of a suitable size as for example 15 to 30 milliliters and preferably approximately 20 milliliters. The space 41 can be evacuated to a vacuum below ambient or atmospheric or a sub-ambient pressure ranging from 15" to 20" of mercury.

The adapter 14 consists generally of a cylindrical body 46 which can be formed of a suitable material such as a transparent plastic, i.e. a polycarbonate or an acrylic. The body 46 is provided with proximal and distal extremities 47 and 48. The distal extremity 48 is necked down as shown in FIG. 1 and is adapted to be removably mounted on the hub 31 of the body 26 to form a fluid-tight seal therewith. Cooperative mating means is provided on the proximal extremity 48 of the body 46 and on the vacuum container 13. Thus as shown in FIG. 1 the proximal extremity 47 is provided with a cylindrical recess 51 which is adapted to receive the vacuum container 13. A flow passage 52 is provided extending from the cylindrical recess 51 through the distal extremity 48 so that it is in communication with the conical recess 29 of the aspiration needle 12.

Needle means is carried by the adapter body 46 for establishing a connection between the flow passage 52, the interior of the vacuum container 13 first for supplying a vacuum to the flow passage 52 and thereafter to break the vacuum being supplied to the flow passage 52. Such needle means is shown in FIG. 1 and consists of first and second needles 53 and 54 formed of a suitable material such as stainless steel. As shown, the first and second needles 53 and 54 are carried by the body 46 and are disposed within the passage 52. The first needle 53 is mounted in a resilient plug or block 56 frictionally retained in the flow passage 52 of the body 46 and formed of a suitable material such as plastic through which the first needle 53 extends. The first needle is provided with a flow passage 57 which extends from a proximal sharpened tip 58 to a distal extremity 59 extending through the plug 56 and opening into the flow passage 52 in the body 46.

The second needle 54 is provided with a proximal extremity 61 and a distal extremity 62. As shown particularly in FIGS. 1 and 2, the second needle 54 is sized so that it can be coaxially mounted on the exterior of the first needle 53 and form an annular flow passage 63 extending from the proximal extremity 61 to the distal extremity 62 and opening into a chamber 66 that is defined by annular shoulders 67 and 68 and which is open to the atmosphere through a hole 71. As can be seen, the proximal extremity 61 of the second needle 54 is sharpened as shown and is distal of the proximal extremity 58 of the first needle 53 by a suitable distance as for example ½" for a purpose hereinafter described. The second needle 54 is supported on the first needle 53 in a suitable manner such as by use of an adhesive or solder 72 within the annular passage 63 as shown particularly in FIG. 2.

Yieldable means in the form of a spring 76 is provided within the chamber 66 and has a larger distal or base end 77 engaging the shoulder 68 and retained in engagement therein by suitable means such as an adhesive 78. The smaller or proximal end 79 of the spring 76 yieldably engages the diaphragm or membrane 39 so as to retain the membrane or diaphragm 39 out of engagement with the sharp end of the first needle 53.

Operation and use of the aspiration needle apparatus 11 may now be briefly described. Let it be assumed that it is desired to perform an aspiration procedure after a physician or surgeon has found a palpable breast tumor by utilizing the apparatus of the present invention for obtaining a cell sample from the breast tumor by withdrawing aspirate from the breast tumor. The apparatus 11 is assembled with the adapter 14 inserted into the conical recess 32 of the needle. The vacuum container 13 is disposed in the adapter 14 with the proximal extremity 58 of the needle 53 distal of the membrane 39 as shown in FIG. 1. The surgeon using one hand for locating the palpable breast tumor utilizes the other hand to grasp the aspiration needle apparatus 11 by two fingers as for example the thumb and forefinger to grasp the annular recess 33 of the aspiration needle 12 and pushes the needle to penetrate the skin of the breast and to enter into the breast tissue and to lodge the distal extremity of the aspiration needle 12 within the tumor. As soon as the surgeon is assured that the needle 12 is lodged into the appropriate position with the tumor.

The surgeon or physician using the forefinger of the hand holding the aspiration needle apparatus 11 engages the vacuum container 13 and presses it distally against the force of the spring 76 to cause relative movement between the adapter 14 and the vacuum container 13 to a first position to cause the sharpened proximal extremity 58 of the first needle 53 to puncture the diaphragm or membrane 39 carried by the container 36 to expose the evacuated space 41 to the interior flow passage 57 of the first inner needle 53 (see FIG. 4). This in turn exposes the flow passage in the body 46 and the conical chamber 29 in the aspiration needle 12 and the flow passage 21 in the elongate tubular member 16 to create a sub-ambient condition within the tumor to cause cells of the tumor to be withdrawn from the tumor as an aspirate into the flow passage 21 and to bring the aspirate into the chamber 29 where the entrance of the aspirate into the chamber can be observed visually through the magnifying lens framed by the spherical portion 26a as shown in FIG. 1.

As soon as it has been ascertained that sufficient aspirate has been drawn into the chamber 29, the sub-ambient pressure being applied to the rigid elongate tubular member can be terminated or broken by the physician pushing the vacuum container 13 in the form of a vacuum bottle 36 and additional distance proximally against the force of the yieldable spring 76 to a second position so that the second needle 54 has its proximal extremity 61 penetrating through the diaphragm 39 as shown in FIG. 5. As soon as the proximal extremity 61 penetrates into the space 41, atmospheric air can enter into the space passing through the hole 71 in the body 46 and into the annular flow passage 63 in the second needle 54 and into the space 41. Thus it can be seen as soon as the second needle 54 punctures the diaphragm 39 the sub-ambient pressure applied to the aspiration needle 12 will be abruptly terminated so that no further aspirate is withdrawn from the tumor.

When the cell sample has been collected in the aspirate within the chamber 29, the aspirate remains within the chamber 29. As soon as the desired cell sample has been collected, the aspiration needle 12 can be withdrawn from the tumor with the adapter 14 and the vacuum container in place. Alternatively if desired, the adapter 14 containing the vacuum container 13 can be removed before withdrawing the aspiration needle 12.

Thereafter, the aspiration needle 12 can be handled in the manner hereinbefore described in connection with the copending application Ser. No. 08/228,551 filed Apr. 15, 1994. As described therein, the aspirate can be discharged onto slides which are shipped to laboratory for analysis or alternatively, the entire needle with the cell sample with the aspirate therein can be supplied to the laboratory for analysis. Thus, as shown in FIG. 6, the aspiration needle 12 with the collected cell sample therein can be placed in a test tube-like container 86 formed of a suitable material such as plastic and sealed with a removable cap 87 for transportation to a laboratory for analysis.

Another embodiment of an aspiration needle apparatus incorporating the present invention is shown in FIGS. 7 and 8. As shown therein, the needle aspiration apparatus 101 consists of aspiration needle 12 identical to that hereinbefore described and a vacuum container 102 and an adapter 103. As shown, the vacuum container 102 can be in the form of a metal canister or container that is in the form of an elongate cylinder and having an internal cylindrical portion 102a disposed coaxially therein. The cylindrical portion 102a defines a cylindrical chamber or recess 107 extending axially of the cylindrical portion 102a which opens through an opening 108 open to the atmosphere provided in one end of the metal container 102. The other end of the cylindrical recess 107 is open through an opening 109 into an interior evacuated annular space 111 in the vacuum container 102 through a self-sealing diaphragm or membrane 112 mounted therein by suitable means such as an adhesive (not shown) to close off that end of the cylindrical recess 107. The cylindrical recess 107 is sized so it can serve as a female adapter for receiving the cylindrical male adapter 103 in the form of a cylindrical body 114 formed of a suitable material such as a transparent plastic of the type hereinbefore described and is provided with the proximal and distal extremities 116 and 117. It is provided with a flow passage 118 extending from the proximal extremity 116 to the distal extremity 117. It is also provided with an additional flow passage 119 that is generally parallel to the passage 118 and extends from the proximal extremity to a point intermediate the proximal and distal extremities 116 and 117 and is in communication with a sidewise extending port 121 that is positioned so it is always open to the atmosphere for a purpose hereinafter described.

A first needle 126 formed of a suitable material such as stainless steel which has a sharpened tapered proximal extremity 127 and a distal extremity 128 is disposed within the flow passage 118 and is retained therein in a suitable manner such as by an adhesive (not shown). The first needle 126 is provided with a flow passage 129 that extends from the proximal extremity 127 to the distal extremity 128 of the needle and opens into the flow passage 118. Similarly, a second needle 131 having a sharpened proximal extremity 132 and a distal extremity 134 is mounted within the body 114 by suitable means such as an adhesive (not shown). It has a flow passage 133 extending from the sharpened proximal extremity 132 to the distal extremity 134 which is in communication with the flow passage 119 that opens to the atmosphere through the port 121 as hereinbefore described. As shown in FIG. 7, the proximal extremities 116 and 127 of the first and second needles 126 and 131 are staggered so that the first needle 126 extends proximally for a suitable distance as for example approximately ¼ to ½" beyond the proximal extremity 127 so that the first and second needles 126 and 131 can sequentially penetrate the diaphragm 112 as hereinafter described. The proximal extremity of the body 116 is tapered as shown so that it can make a tight friction fit with the hub 31 of the aspiration needle 12 to provide a fluid-tight seal therebetween.

A conical coil spring 136 is disposed within the cylindrical recess 107 and is secured therein by suitable means such as an adhesive (not shown) and extends distally from the diaphragm 112 and is adapted to be engaged by the adapter 103 when it is inserted into the cylindrical recess 107. The coil spring 136 serves to prevent inadvertent puncturing of the diaphragm 112 by the first and second needles 126 and 131.

Operation and use of the aspiration needle apparatus 101 as shown in FIGS. 7 and 8 is very similar to that shown in FIG. 1 with the exception that the vacuum container 13 shown in FIG. 1 is in the form of a male member adapted to mate with an adapter 14 which is constructed as a female member providing a chamber 66 for receiving the vacuum container 13. Conversely, with the embodiment shown in FIGS. 7 and 8, the vacuum container 102 is constructed as a female member having a cylindrical recess 107 therein adapted to receive an adapter 103 which is constructed in the form of a male member adapted to mate with the cylindrical recess 107. Thus, as can be seen in the arrangement shown in FIG. 1, the first and second needles 53 and 54 are coaxially disposed with respect to each other whereas in the embodiment shown in FIG. 7, the first and second needles 126 and 131 are disposed side by side.

In operation of the apparatus shown in FIGS. 7 and 8, when the aspiration needle has been positioned so that the distal extremity 18 of the aspiration needle 12 is disposed within the tumor, the vacuum container 102 can be pressed forwardly or proximally against the force of the conical coil spring 136 to a first position to cause the proximal extremity 127 of the first needle to penetrate the diaphragm 112 and to expose the aspiration needle 12 to the sub-ambient pressure provided in the vacuum container 102 to cause aspirate to be drawn into the chamber of the aspiration needle 12 in the manner hereinbefore described. When a sufficient sample has been collected, the vacuum container 102 can be further depressed to cause the proximal extremity 132 of the second needle 132 to puncture the diaphragm to expose the evacuated space 111 in the vacuum container 12 to ambient through the port 121 to break the sub-ambient condition being applied to the aspiration needle 12 to thereby terminate collection of aspirate. Thereafter, the needle aspiration apparatus 101 can be removed and the sample collected in the aspiration needle treated in the manner hereinbefore described.

It is apparent from the foregoing that there has been provided an aspiration needle apparatus 11 which facilitates collection of aspirate and cell samples as for example in tumors and the like. This collection is enhanced because it eliminates the necessity for the physician or surgeon doing the procedure to utilize a syringe or other vacuum source to create the necessary sub-ambient condition in the aspiration needle. By utilizing a pre-packaged vacuum container to supply the desired sub-ambient condition to the needle for an appropriate period of time, the collection of the appropriate cell sample is greatly enhanced. Thus it is possible to readily collect cell samples without the necessity of having a syringe or other accessory devices as for example a vacuum pump to supply the sub-ambient condition. Also by providing a vacuum container having a predetermined volume of evacuated space, it is possible to program the sub-ambient pressure applied to the aspiration needle 12 to also predetermine the maximum amount of time that a sub-ambient pressure will be applied to the aspiration needle. In addition, the aspiration needle apparatus of the present invention is relatively simple. It can be readily manufactured. If desired, it can be supplied in kit form.

Still another embodiment of the aspiration needle apparatus incorporating the present invention is shown in FIGS. 9 and 10. The aspiration needle apparatus 151 consists of an adapter 152 which can be formed of a suitable material such as plastic. The adapter 152 consists of a body 153 which is provided with a cylindrical bore 154 sized to receive either a small vacuum container 156 shown in FIG. 11 or a large vacuum container 157 shown in FIG. 12. Both of the vacuum containers 156 and 157 are cylindrical as shown and have basically the same diameter with the large vacuum container 157 having a greater length than the small vacuum container 156. The evacuated space 158 in the small vacuum container 156 can be of a suitable size as for example 20–30 milliliters, whereas the evacuated space 159 in the large vacuum container 157 can be of a suitable size as for example 30–60 milliliters. These evacuated spaces are accessible by a needle which can penetrate penetrable diaphragms 161 and 162, respectively which seal the containers. As shown in FIG. 9, the bore 154 in the body 153 forms a cylindrical sleeve 166 into which the vacuum containers 156 and 157 can be inserted.

Needle means 171 is carried by the body 153 of the adapter 152 and has a proximal extremity 172 which extends into the bore 154 that serves as a penetrating needle and a distal extremity 173 extending distally of the body 153 which serves as an aspiration needle. A cell collection chamber 176 is provided as a part of the needle means and is disposed between the proximal and distal extremities 172 and 173 of the needle means. It is possible that the needle means 171 be formed as a single needle of a suitable material such as stainless steel. However, in accordance with the present invention it is preferable to form the needle means with the distal extremity 173 being a separate aspiration needle of the type hereinbefore described and the proximal extremity 172 being formed as a separate penetrating needle also of the type hereinbefore described. When formed as separate needles, the needles can be embedded within the body 153 and having the flow passages therein in communication with a flow passage 181 in communication with the cell collection chamber 176 which also can be formed in the tapered conical extension 182. As previously disclosed, the conical extension 182 can be provided with a convex portion 183 which surrounds the cell collection chamber 176 to provide magnification means for viewing the cell sample collected within the cell collection chamber 176. Thus the flow passage in the distal extremity 173, the cell collection chamber 176 and the flow passage 181 are in communication with the flow passage in the proximal extremity 172 and in communication with the interior of the sleeve 166. Yieldable means in the form of a foam rubber disc 186 is provided within the bore 154 and has a bore 187 therein through which the proximal extremity 172 of the needle means 171 extends. It is generally preferable that the proximalmost extremity of the proximal extremity 172 of the needle means 171 protrude slightly above the proximal surface of the yieldable means 186.

The apparatus shown in FIG. 9 can be used with a medium bottle or container 191 such as shown in FIG. 13 in which the medium is carried within the bottle and is accessible through a cap 193 threaded onto the bottle and having a penetrable diaphragm 194 carried thereby giving access to the medium 192.

Operation and use of the aspiration needle apparatus shown in FIGS. 9 through 13 may now be briefly described as follows. The physician picks up the adapter 152 and places the small vacuum container 156 within the bore 154 of the sleeve 166 with yieldable means 186 serving to prevent the proximal extremity 172 of the needle means 171 from penetrating the diaphragm 161. The physician, while holding the adapter 152 in one hand utilizes the other hand to localize the lump which is to be analyzed and keeps it in position while the other hand is utilized to cause the distal extremity 173 of the needle means 171 to penetrate the lump within the tissue. If desired, ultrasound can be utilized for aiding and locating the lump to be analyzed. As shown in FIG. 15, the distal extremity 173 has been positioned within a lump 201 in tissue 202.

As soon as the distal extremity 173 of the needle means 171 has been properly positioned within the lump 201, the forefinger 206 of the hand holding the adapter 152 can be used to urge the small vacuum container 156 inwardly against the force of the yieldable means 186 to cause the proximal extremity 172 to penetrate the diaphragm 161 to establish communication with the evacuated space 158 and the flow passage in the needle means so that a vacuum is supplied to the distal extremity 173 disposed within the lump or tumor 201. The needle means 171 is kept steady by the physician's index finger and thumb while maintaining the vacuum condition and the needle means 171 by the forefinger continuously applying pressure to the small vacuum container 156. By holding the adapter 152 in this manner, it is possible for the physician to gently pass the distal extremity 173 back and forth through the tumor to ensure that an adequate cell sample has been collected which can be ascertained by viewing the collection of the cell sample in the collection chamber 166 through the magnifying bulb 183.

As soon as an adequate cell sample has been collected, the vacuum being applied to the needle means 171 is terminated by the forefinger releasing the small container 156 permitting the yieldable means 186 to urge the small vacuum container 156 axially away from the proximal extremity 172 of the needle means 171. The distal extremity 173 of the needle means 171 is then removed from the tissue 202 of the patient. The small vacuum container 156 is removed from the bore 154 and the large vacuum container 157 is placed in the bore 154 of the sleeve 166 as shown in FIG. 15. The distal extremity 173 of the needle means 171 is then covered to penetrate the diaphragm 194 of the medium container 191. As soon as the distal extremity 173 is submerged within the medium 192, the large vacuum container 157 can be pressed by the forefinger of the hand to cause the proximal extremity 172 to penetrate the diaphragm 172 to couple the evacuated space to the flow passage in the needle means 171 to suck up medium 192 to the flow passage into the needle means and to carry with it the cell sample collected within the collection chamber 176 and to bring the collected cells along with the medium into the interior of the vacuum container 157. As soon as the cell sample has been collected from the cell collection chamber, the large vacuum container 157 can be released by the forefinger permitting the yieldable means 186 to urge the large vacuum container off of the proximal extremity 172 of the needle means to interrupt supplying of a vacuum to the needle means 171.

The large vacuum bottle 157 containing the cell specimen along with medium can then be removed from the sleeve 166 and then shipped to a laboratory where the collected cells can be evaluated.

It can be seen from the foregoing that there has been provided an aspiration needle apparatus that is very simple in construction and can be readily used for collecting cell samples. The cell sample collected in the collection chamber of the needle means can be readily removed from the needle means by use of a second vacuum container and sucking the cell collection from the collection chamber by sweeping the cell collection out by the use of a medium also aspirated into a large vacuum container for later shipment to a laboratory for analysis. This eliminates the need to supply a needle with the cell collection therein to a laboratory. It also eliminates the need for a double lumen needle of the type hereinbefore described.

It should be appreciated that it is possible if there is a large enough vacuum container available to utilize a single vacuum container for performing the aspiration and collection functions hereinbefore described by the small and large vacuum containers. However, it may be undesirable to use a single vacuum container because there is a possibility of air being introduced into the vacuum container as the cells are being collected from tissue of the patient. It can be seen that a flow passage construction has been provided for the collection of the cells so that cells will not become entrapped in the needle means. Also it can be seen that the needle aspiration apparatus of the present invention is very simple and inexpensive and greatly facilitates the collection of cell samples free of contamination.

In connection with the embodiment of the apparatus of the present invention shown in FIGS. 9–15, it has been found that the use of one finger by the physician holding the back end of the vacuum container to push it down into engagement with the needle during the aspiration process may at times be awkward to the physician because that finger cannot be utilized for holding and steadying the sleeve-like adapter during aspiration, particularly when the needle is disposed within the tumor and is being moved back and forth to collect the cell sample. Thus there has been provided an embodiment of the invention shown in FIGS. 16–20 which includes an on-off mechanism in the adapter making it possible to establish a vacuum merely by one movement of the finger against the vacuum container and which maintains this vacuum until it is desired to terminate the vacuum, after which the vacuum bottle can be again pressed to cause termination of the vacuum.

The aspiration needle apparatus 221 shown in FIGS. 16–20 consists of a 23-gauge stainless steel needle 222 of the type hereinbefore described in which the distal extremity is in the form of a sharpened point 223 and the proximal extremity 224 is encapsulated within a body 226 formed of a suitable material such as a transparent plastic of the type hereinbefore described. The body is provided with a conical chamber 227 which is provided with a taper of approximately 1.7° and a length of 0.375". The chamber 227 extends into another conical chamber 228 having a side wall extending at 5.2° and a length of 0.200". The chamber 228 terminates at the proximal extremity of the needle 222. The body 226 is provided with a generally spherical or convex portion 231 surrounding the chamber 228 and serving as magnifying means in the manner hereinbefore described to facilitate witnessing the collection of cell samples as they enter into the chamber 228. The body 226 is provided with a cylindrical protrusion 232 extending distally from the spherical portion 231 and adjoins a smaller diameter distally extending cylindrical protrusion 233 which is adapted to frictionally receive a protective sleeve 236 formed of a suitable material such as transparent plastic. The sleeve 236 has a length which is longer than the length of the needle 222 to prevent accidental engagement with the sharpened tip 223. The sleeve 236 is seated against the cylindrical protrusion 232 while being frictionally retained by the cylindrical protrusion 233. A Luer-type fitting 238 is provided on the proximal extremity of the body 226 as for example a female Luer fitting which is adapted to mate with a corresponding male Luer fitting 241 of an adapter 242. The adapter 242 carries a cylindrical open-ended sleeve 243 which is adapted to receive a vacuum container 246 of the type hereinbefore described. A second sharpened needle 251 of the type hereinbefore described has its distal extremity mounted within the Luer fitting 241 as shown and opens into the Luer fitting so that when the Luer fittings 241 and 238 are mated, the flow passage in the needle 251 is in communication with the chamber 227 and the flow passage within the needle 222. The proximal extremity of the needle 251 is provided with a sharpened tip 252. The vacuum container 246 of the type hereinbefore described has an enclosed evacuated space evacuated to a subambient pressure sealed by a penetrable diaphragm 256 adapted to be penetrated by the needle 251.

In accordance with the present invention, an on-off mechanism, which also may be called a click-on click-off mechanism 261 is provided within the adapter 242 for controlling movement sequentially from a first depressed, forwardmost or "on" position and a second released, rearwardmost or "off" position. The on-off mechanism 261 consists of a circular disk 262 which is slidably mounted for axial movement within the cylindrical recess 263 provided in the sleeve 243. The circular disk 262 is guided during its travel within the cylindrical recess 263 by a depending leg 264 formed integral therewith that extends at right angles to the plane of the circular disk 262 and is offset from the center so that it can travel in an elongate recess 266 provided in the wall of the sleeve 243 formed in the cylindrical recess 263. The cylindrical disk 262 is provided with a hole 268 through which the needle 251 can extend. The cylindrical disk 262 is also provided with an axially extending boss 269 frictionally retained in the hole 268 through which a hole 270 extends. The needle 251 can freely travel through the hole 270.

The cylindrical recess 263 terminates at the bottom wall 271 which extends at right angles to the wall forming the cylindrical recess 263 and has formed integral therewith an axially extending protrusion 272 centrally disposed thereon and which is provided with a bore 273 through which the needle 251 extends. The protrusion or boss 272 is axially aligned with the boss 269 and serves for retaining opposite ends of yieldable spring means in the form of a helical coil spring 276 that serves to yieldably urge the disk 262 in a direction away from the bottom wall 271. The coil spring 276 has sufficient strength so that when the vacuum container 246 is released by the hand depressing it, the coil spring 276 will cause the disk 262 to move sufficiently so that the needle 251 no longer penetrates the diaphragm 256.

On-off latch or detent means 281 forms a part of the on-off mechanism 261. The on-off latch or detent means 281 takes the form of a grooved pattern 282 extending through the inwardly facing surface 283 of the depending leg 264 carried by the disk 262. This grooved pattern 282 is engaged by a wire-like L-shaped spring member 284 having one leg 286 embedded within the bottom wall 271 and having the other leg 287 extending substantially at right angles thereto. The leg 287 is a much shorter leg than the leg 286 and yieldably engages the grooved pattern 282. Additional yieldable means is provided in the form of a leaf spring 291 formed of a suitable material such as tempered steel. The leaf spring 291 has one portion 291a which is seated on the boss 272 and another end 291b which is inclined outwardly towards the wall forming the cylindrical recess 263 and into engagement with the leg 286 to apply an additional yieldable spring force to maintain the leg 287 in engagement with the grooved pattern 282.

The grooved pattern 282 engaged by the leg 287 of the spring member 284 as shown in FIG. 18 is in a position in which the disk 262 is in its outermost position with the vacuum container 246 disengaged from the needle 251. The configuration of the grooved pattern 282 can be best explained in conjunction with movement of the circular disk 262 relative to the leg 287 of the spring member 284. In the position of the leg 287 shown in FIG. 18, the leg 287 is disposed in the lowermost extremity of an inclined groove 296 to serve as stop means which prevents the disk 262 from being urged outwardly through the cylindrical recess beyond a predetermined distance. As the disk 262 is depressed inwardly under the force of the vacuum container 246, the grooved pattern 282 carried by the leg 264 causes the leg 287 to follow and move sideways in the angularly extending groove 296 and move vertically in an adjoining groove 297 after which it moves into another adjoining angularly extending groove 298. However, at the transition between the groove 297 and 298, there is a step 299 because the groove 298 has a depth which is greater than the groove 297. When the container 246 is released by the hand, the spring 276 urges the disk 262 and the leg 264 carried thereby outwardly causing the leg 287 to travel sideways towards the center of the grooved pattern 282 until it comes into engagement with another groove 301 extending at an angle as for example approximately 90° with the groove 298. Since the groove 301 has a depth which is greater than the groove 298, there is a step 302 in the transition from groove 298 to groove 301 over which the leg 287 travels.

During this movement of the disk 282 under the urging of the container 246, the needle 251 penetrates the membrane or diaphragm 256 of the vacuum container 246 to supply a vacuum to the needle 251 as hereinafter described. Let it be assumed that it is now desired to terminate this vacuum. Upon depression of the container 246 by the hand which causes movement of the disk 262 with the depending leg 264 inwardly of the cylindrical recess 263, the leg 287 will travel up the groove 301. It will not travel up the groove 298 because it has dropped over the step 302. The leg 287 moves sidewise into a groove 303. In movement of the leg 287 from the groove 301 to the groove 303, another step 304 occurs because the groove 303 has a depth greater than the groove 301 preventing the leg 287 from returning in groove 301. As the container 246 is released, the coil spring 276 will urge the disk 262 outwardly and axially in the cylindrical recess 263 causing the leg 287 to travel downwardly along the groove 303 and thence into an adjoining angularly extending groove 306 until it again comes into engagement with the adjoining groove 296. In moving from the groove 306 to the groove 296 another step 307 is encountered at that junction because the groove 296 has a depth which is greater than the depth of the groove 306, thus preventing the leg 287 from traveling up the groove 306 when the container 246 and the disk 262 are again depressed.

From the foregoing it can be seen that the grooved pattern is one that only permits one direction of travel of the leg 287 through the maze provided by the grooved pattern 282 thus assuring that when the vacuum container 246 is pushed to its depressed, forwardmost or "on" position, the needle 251 will penetrate the diaphragm 256 of the vacuum container 246 and be exposed to the subambient or vacuum pressure within the vacuum container 246 and retained therein when the leg 287 is disposed in the upper apex of the grooved pattern formed by the junction of the grooves 298 and 301. The next time that the vacuum container 246 and the disk 262 are depressed, the leg 287 moves out of the upper apex and is released permitting the coil spring 276 to yieldably urge the disk 262 and the container 246 disposed within the sleeve 236 to be moved into a released, rearwardmost or "off" position so that the needle 251 no longer penetrates the diaphragm 256 and is free of the diaphragm 256 thereby terminating the application of a subambient or vacuum condition applied to the needle 251. The leg 287 thereafter moves into the lower apex of the grooved pattern 282 formed by the junction of grooves 306 and 296. Because the on-off mechanism hereinbefore described emits an audible sound during movements between the two apices of the on-off mechanism, it can be characterized as a click-on click-off mechanism.

Operation and use of the apparatus shown in FIGS. 16-20 may now be briefly described as follows. In general the operation and use of the apparatus is very similar to that hereinbefore described with the previous embodiments with the exception that the on-off mechanism 261 makes it unnecessary to continue to hold the vacuum container 246 during the time the aspiration procedure is taking place. The needle 222 after removal of the protective sleeve 236 is inserted through the skin and passed into the tumor. As soon as it has been determined that the needle 222 has entered the tumor in the appropriate location, aspiration of the cells from the tumor can be commenced by supplying subambient pressure to the needle 222 by depressing the vacuum container 246 with one finger of the hand and urging it inwardly against the force of the spring 276 into the depressed, forwardmost or "on" position to cause the needle tip 252 to penetrate the diaphragm 256 of the container 246 to supply the subambient condition within the container 246 to the needle 251 which causes it to be supplied to the adjoining conical chambers 227 and 228 and thence to the needle 222. As soon as the circular disk 262 has reached its innermost position in the cylindrical recess 263, the vacuum container 246 can be released by the hand and the latching or detent mechanism 281 serves to retain the vacuum container 246 in a first or "on" position. In order to aid in the aspiration of cells, the needle 222 can be progressively moved back and forth within the tumor until aspirated cells can be seen in the tapered chamber 228 through the spherical lens 231. As explained in co-pending application Ser. No. 08/421,064 filed Apr. 23, 1995, the collection of such cell samples can be enhanced by imparting vibratory motion to the needle 222 electromechanically. By providing the detent or latching mechanism 281, the physician may remove his finger from the container 246 and utilize that finger in conjunction with the hand to carry out the desired movements of the adapter 242 and the needle 222 carried thereby to enhance the cell collection.

As soon as the physician determines that sufficient collection of cells has been obtained by observation through the spherical portion 231 serving as a lens, aspiration can be terminated by utilizing a finger of the hand and depressing the vacuum container 246 against the force of the coil spring 276. This causes the leg 287 to move out of the recess 301 and to move over the step 304 into the groove 302 permitting the coil spring 276 to move the member or disk 262 to a released, rearwardmost or "off" position in which the leg 287 is seated in the groove 296 to hold the disk 262 in the released position. As this is occurring, the needle 251 is withdrawn from the vacuum container 246 and from the diaphragm 256 to break the supply of a subambient pressure to the needle 251 and thence to the needle 222.

The aspiration needle 222 can then be removed from the patient and the cell sample collected can be treated in the manner hereinbefore described. For example, it can be collected in the same or a different vacuum container 246 as hereinbefore described by placing the aspiration needle below the surface of a medium in another bottle. The vacuum container 246 can then be depressed with a finger of the hand to reestablish the subambient pressure or vacuum condition to cause a medium in the bottle to be sucked up with the cell specimen collected in the chambers 227 and 228. As soon as sufficient medium has been brought through the needle 222 to flush the cells collected into the vacuum container, the subambient pressure can be terminated by again depressing the vacuum container 246 against the force of the spring 276 to release the leg 287 of the spring 284 from the upper apex of the grooved pattern 282 and permitting the spring to return to the inner apex of the grooved pattern 282 and removing the needle 251 from the diaphragm 256. The vacuum container containing the cell sample and the medium can then be sent to the laboratory for analysis.

From the foregoing it can be seen that the detent or latching mechanism 281 provided makes it possible for the physician using the apparatus to release the vacuum container 246 after each operation, greatly aiding the physician in the handling of the adapter 242 and the needle 222 carried thereby to carry out the cell collection procedures.

From the foregoing it can be seen that there has been provided an essentially auto-aspirating apparatus which includes a self-contained vacuum or subambient condition. With the apparatus of the present invention it is possible to visualize a specimen as it is being collected in the chamber therefore making it very easy to ascertain when sufficient cell specimens have been obtained. The on-off mechanism makes it easy to establish, maintain and break a vacuum.

It should be appreciated that the present apparatus can be utilized for collecting cells other than tumor cells. For example, cells can be collected to establish a baseline reference before a cancerous condition is established. When longer needles are utilized, various types of tissue can be analyzed within the body, as for example lungs, liver, pancreas and other organs of the body. All that is required is a longer needle.

The use of the on-off mechanism in the adapter makes it easier for the adapter and the needle carried thereby to be operated by one hand with a single finger being periodically utilized to actuate the manual on-off mechanism to supply subambient pressure to the needle or alternatively to break the supply of a subambient pressure to the needle. With this on-off mechanism, the apparatus is more user friendly and makes it possible to obtain larger numbers of cells in the cell samples and to improve the quality of cells in the cell samples. This is made possible because there is no entrapping of the cell specimen in the hub of the needle. The specimen can be readily visualized during the aspiration procedure. The interior of the needle is smooth with no sharp edges, thereby minimizing trauma to the cells as they are collected.

We claim:

1. An aspiration needle apparatus for collecting cell samples from tissue comprising a vacuum container having an enclosed evacuated space evacuated to a subambient pressure and sealed by a penetrable diaphragm, an adapter having a recess to receive said vacuum container, needle means carried by the adapter and having a distal extremity serving as an aspiration needle to collect the cell sample and having a proximal extremity disposed in said recess and being capable of penetrating the diaphragm of the vacuum container to couple the evacuated space to the flow passage of the needle means to supply a subambient pressure to the distal extremity of the needle means, an on-off mechanism carried by the adapter including a member mounted in the recess for axial movement in the recess and engaged by the vacuum container, yieldable means disposed within the recess and engaging said member and yieldably urging said member and the vacuum container in a direction out of the recess and detent means secured to said member for sequentially retaining said member in a first forwardmost position and a second rearwardmost position whereby in the first forwardmost position the needle means penetrates the diaphragm to supply a subambient pressure to the needle means and in the second rearwardmost position the needle means is free of the diaphragm so that subambient pressure is no longer supplied to the needle means.

2. Apparatus as in claim 1 wherein said needle means includes a collection chamber disposed between the proximal and distal extremities of the needle means.

3. Apparatus as in claim 2 together with magnification means carried by the needle means for magnifying an interior of the collection chamber.

4. Apparatus as in claim 1 where said yieldable means disposed within the recess yieldably retains the vacuum container out of engagement with the proximal extremity of the needle means.

5. Apparatus as in claim 1 wherein said detent means includes a spring member having an inwardly facing leg and a grooved pattern carried by a disk and wherein said spring member has a portion thereof adapted to seat in said grooved pattern and means for causing relative movement between the leg of the spring member and the grooved pattern as the spring member is moved in the recess.

6. Apparatus as in claim 1 wherein said grooved pattern is in the form of a one-way maze permitting movement of the leg of the spring member in only one direction in the maze.

7. An adapter for use with an aspiration needle and a vacuum container for supplying subambient pressure to the aspiration needle from the vacuum container, the vacuum container having an evacuated space therein evacuated to a subambient pressure and a puncturable diaphragm providing access to the evacuated space comprising a body having a cylindrical open-ended recess therein adapted to receive the vacuum container, a needle mounted in the body and extending into the recess axially thereof, a member slidably mounted in the recess and adapted to be engaged by the vacuum container, means disposed within the recess and yieldably urging the member in a direction out of the recess and detent means connected between the member and the body for terminating movement between first and second positions and for retaining said member sequentially in said first and second positions and in the first position permitting the vacuum container to engage the member and permitting movement of the diaphragm of the vacuum container onto the needle as the member is moved to the second position from said first position and thereafter in sequence upon depression of the vacuum container permitting the member and the vacuum container engaging the same to be moved to the second position with the needle out of engagement with the diaphragm.

8. An adapter as in claim 7 together with an additional needle having a proximal extremity and a sharpened distal extremity and a mating coupling carried by the proximal extremity, said adapter including a coupling adapted to mate with the coupling on the additional needle and to place the additional needle in communication with the needle in the adapter whereby when a subambient condition is applied to the needle in the adapter the subambient condition is also supplied to the additional needle.

9. A method for withdrawing aspirate from tissue in a body by the use of an aspiration needle and a vacuum container having an evacuated space therein evacuated to a subambient pressure accessible through a puncturable diaphragm, the aspiration needle having a needle and a collection chamber and a tubular member having a sharpened distal extremity and a flow passage extending from the distal extremity into the collection chamber and an adapter having a cylindrical recess therein adapted to receive the vacuum container, a member slidably disposed within the recess of the adapter and engaged by the vacuum container, yieldable means carried by the adapter and yieldably urging the member in a direction out of the recess in the adapter, detent means connected between the member and the body of the adapter for limiting movement of the member between a first position and a second position and for retaining said member in either of said first and second positions, a needle carried by the body of the adapter and extending inwardly into the recess and through said member and having a sharpened proximal extremity and a distal extremity, the adapter having a coupling through which the distal extremity of the needle extends for mating with the coupling of the aspiration needle whereby when a subambient condition is supplied to the needle in the adapter the subambient is supplied to the aspiration needle, the method comprising attaching the coupling of the aspiration needle to the coupling of the adapter, placing the aspiration needle in a tumor from which a cell sample is to be collected, depressing the vacuum container to urge the member against the force of the yieldable to cause the needle within the recess in the adapter to penetrate the diaphragm of the vacuum container so that a subambient pressure is supplied to the needle carried by the adapter and to the aspiration needle to aspirate cells from the tumor, releasing the vacuum container and using the hand to cause motion of the adapter to move the aspiration needle into the tumor to enhance the collection of cells from the tumor, observing the cells as they are being collected and terminating the collection of cells by utilizing a finger of the hand to depress the container against the force of the yieldably means in the recess to cause the detent means to permit the member to return to its first position and causing movement of the diaphragm off of the needle to terminate the supplying of a subambient pressure to the aspiration needle.

10. A method as in claim 9 for use with a medium container further comprising the steps of introducing the aspiration needle into the medium and then depressing the vacuum container to urge the member inwardly in the recess to cause the needle in the recess to penetrate the diaphragm to supply a subambient pressure to the aspiration needle so that medium is collected from the medium container and carries with it the collected cells into the vacuum container, depressing the vacuum container after the collected cells have been introduced into the vacuum container and permitting the yieldable means to urge the vacuum container with the diaphragm thereon off of the needle and thereafter shipping the vacuum container to a laboratory for analysis.

* * * * *